US00PP08635P

United States Patent [19]

Barr

[11] Patent Number: Plant 8,635

[45] Date of Patent: Mar. 8, 1994

[54] *RHAPHIOLEPIS INDICA* "HINES DARKLEAF"

[75] Inventor: William C. Barr, Rosenberg, Tex.

[73] Assignee: Hines Nurseries, Inc., Houston, Tex.

[21] Appl. No.: 928,267

[22] Filed: Aug. 10, 1992

[51] Int. Cl.[5] ..... A01H 5/00

[52] U.S. Cl. ..... Plt./67.5

[58] Field of Search ..... Plt. 67.5

*Primary Examiner*—James R. Feyrer

*Assistant Examiner*—Erich E. Veitenheimer

*Attorney, Agent, or Firm*—Christie, Parker & Hale

[57] ABSTRACT

The new plant is a hybrid *Rhaphiolepis indica* plant characterized by its unique deep purple foliage in winter that is a darker purple than any other *Rhaphiolepis indica* cultivar. It is also unique for its compact, low growth habit.

3 Drawing Sheets

BACKGROUND OF THE INVENTION

The present invention relates to a new and distinct plant cultivar of the variety *Rhaphiolepis indica* (L.) Lindl shrub commonly known as "Indiana Hawthorn" in the Rosaceae family. I call this new cultivar by the cultivar name 'Hines Darkleaf'.

This new *Rhaphiolepis indica* selection was discovered in a block of *Rhaphiolepis indica* seedlings during the spring of 1986 as a new found seedling of unknown parentage growing in a cultivated area at a containerized commercial nursery in Houston, Tex. This plant was recognized as distinct from other *Rhaphiolepis indica* cultivars, and was selected and isolated for further evaluation. The new *Rhaphiolepis indica* selection has been reproduced by asexual propagation under my direction at Fort Bend County, Tex., through numerous generations by vegetative cuttings. Successive generations produced in this manner have demonstrated that the novel and distinctive characteristics of this new variety are fixed and hold true under asexual propagation from generation to generation.

This new selection has many desirable and distinctive characteristics which render it unique from other *Raphiolepis indica* cultivars. This new cultivar has the following combination of characteristics which distinguish it from other varieties: Unique deep purplish/black foliage in winter is a darker and deeper purple than that of any other *Raphiolepis indica* cultivar. It is also unique for its compact, low, prostrate growth habit.

My new variety is illustrated in the accompanying photographic drawings which depict the colors of the new variety as nearly true as is reasonably possible to make the same in a color illustration of this character.

DETAILED PLANT DESCRIPTION

Figure 1:
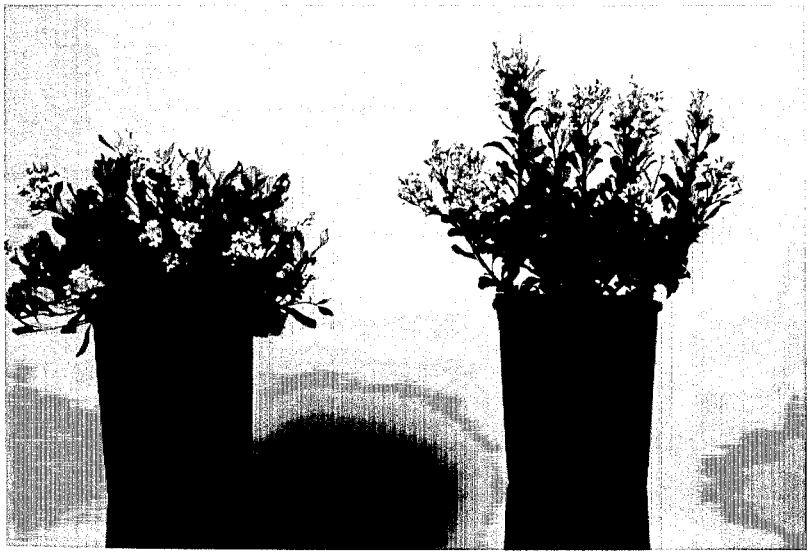
FIG. 1 shows a plant of the 'Hines Darkleaf' cultivar (left photograph in the figure) and a plant of *Rhaphiolepis indica* 'Ballerina' (right photograph in the figure) taken in the spring to show a comparison of these two plants. These two plants were grown under culturally identical conditions (pruning, transplanting, and fertilization). The plants are both two to five years old from cutting to the size shown in the photograph.
Figure 2:
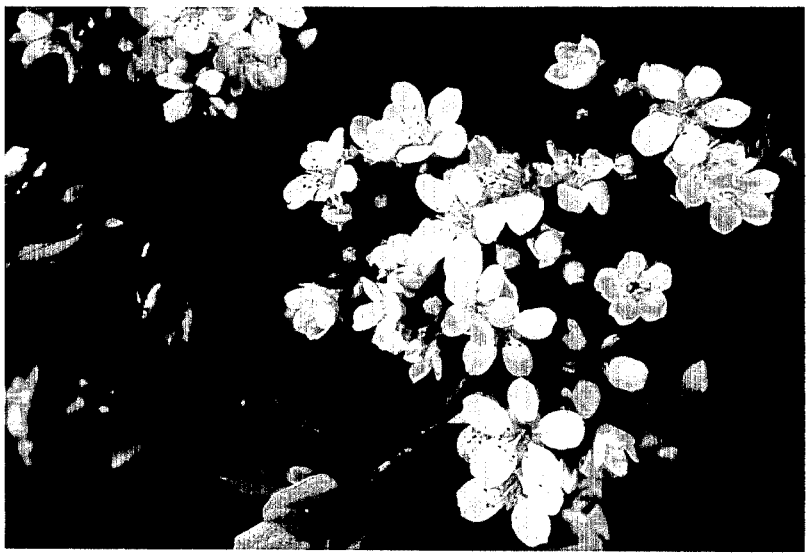
FIG. 2 is a close-up of the flowers of the 'Hines Darkleaf' variety.
Figure 3:
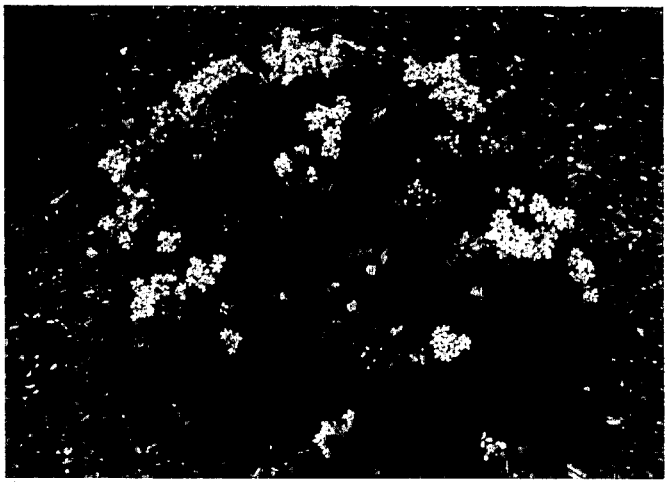
FIG. 3 is a photograph of the cultivar 'Hines Darkleaf' planted in the landscape for approximately one year from a number five container.
Figure 4:
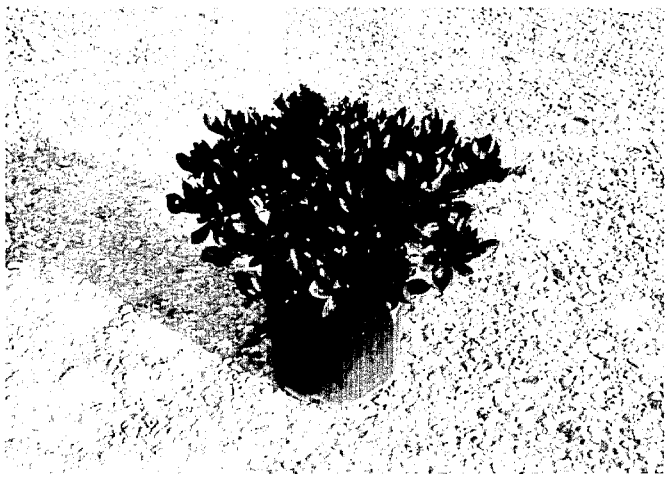
FIG. 4 is a photograph of a 'Hines Darkleaf' plant displaying its winter foliage.
Figure 5:
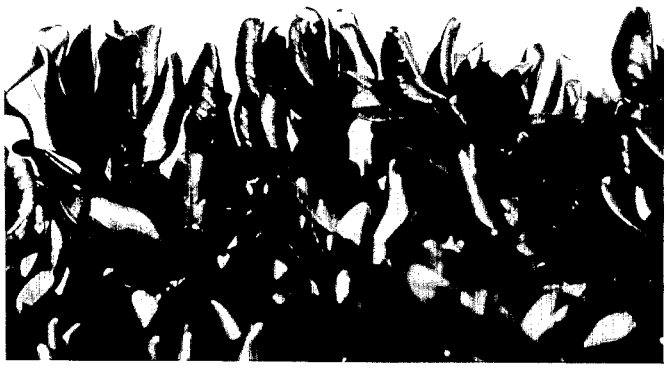
FIG. 5 is a close-up of the winter foliage of the 'Hines Darkleaf' variety.
Figure 6:
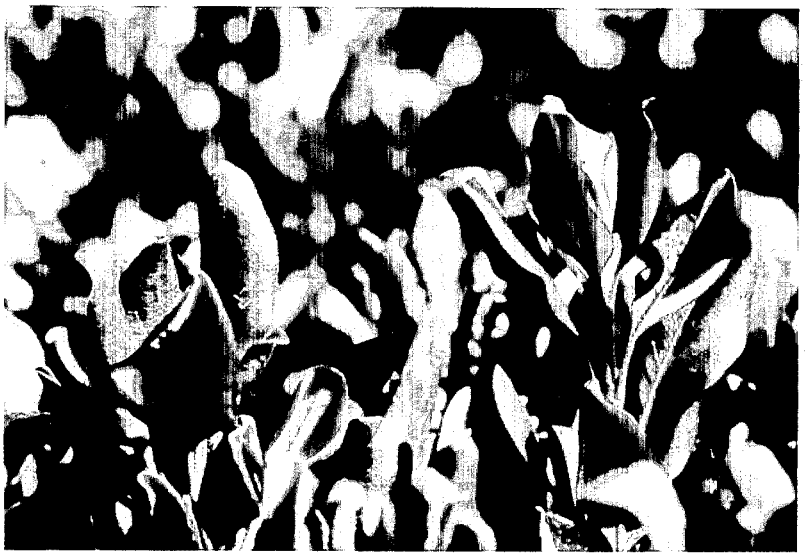
FIG. 6 is a close-up of the spring flush of growth of the 'Hines Darkleaf' variety.

The following is a detailed description of the new *Rhaphiolepis indica* variety. This description is based on observations of no fewer than 20 specimens for each specified characteristic. Color determinations and comparisons are all based on The Royal Horticultural Society Colour Chart. The following descriptions are based upon mature development in Fort Bend County, Tex.

Origin: Hybrid seedling.

Parentage: Unknown.

Classification: Hybrid.

Form: Low, compact, prostrate.

Height: About 61 to 76 cm, spread about 183 cm or more.

Foliage:

- *Apex.*—Cuspidate.
- *Arrangement.*—Alternate.
- *Base.*—Narrow cuneate.
- *Margins.*—Recurved entire.
- *Shape.*—Elliptic to obovate.
- *Surface.*—Glabrous, coriaceous.
- *Juvenile foliage.*—Pubescent.
- *Type.*—Simple.
- *Size.*—Average Length — about 7.5 to 8.8 cm (leaf apex to leaf base); Average Width — about 2.5 to 3.7 cm.

Color:

A. *Winter color.*—1. Upper leaf surface of mature leaves: near to RHS 187A with black undertones. 2. Lower leaf surface of mature leaves: near to RHSA 138A. 3. Upper leaf surface of young (immature) leaves: Tip portion near to RHS 59A, near to 143A at the base of the leaf. 4. Stems are near to 59A. 5. Lower leaf surface of young (immature) leaves: near to RHS Green 143C.

B. *Summer color.*—1. Upper leaf surface of mature leaves: near to RHS 147A. 2. Lower leaf surface of mature leaves: near to RHS 146B with veins near to RHS 137D. 3. Upper leaf surface of young (immature) leaves: near to RHS 178C, changing to near 164A. 4. Lower leaf surface of young (immature) leaves: near to RHS Colour 171A, changing to near to 172B.

Inflorescence: Flowers are in linear panicles average 10.3 cm.

Bloom period: February to late April, peak time March to mid-April; sporadic bloom in September to November.

Petal color: Near to RHS 54C and 155C.

Flower diameter: About 2.1 cm.

Petal shape: Ovate (curled).

Petal number: Five.

Peduncle: About 0.20 cm.

Fruit: Drupelike pome, color near to RHS 202A.

DESCRIPTION OF OTHER POTENTIALLY SIMILAR RHAPHIOLEPIS CULTIVARS

The following descriptions and comparisons are based on an average of not less than twenty specimens for each specified characteristic. The comparisons were formulated from side-by-side evaluation of container grown specimens of each of the specimens listed below. This cultivar was chosen on the basis that it is believed to be the most similar cultivar to 'Hines Darkleaf'. Comparison plants are, as nearly as possible, all the same age and have been grown in the same environment with the same cultural techniques.

*Rhaphiolepis indica* 'Ballerina' (U.S. Plant Pat. No. 2,972)

Flower color: Deep rosy pink, Red-Purple near to 55B.

Plant habit: Compact, mounding upright.

Plant height: 90–120 cm.

Leaf length: About 6.5 cm.

Leaf width: About 2.7 cm.

Leaf margins: Undulated.

Following is a further comparison of these cultivars:

| | 'HINES DARKLEAF' | 'BALLERINA' |
|---|---|---|
| Plant Structure: | | |
| Growth habit | low, compact, prostrate | compact, mounding, upright |
| Overall size | height 2 to 2.5', spread 6' or more | height 3', spread 4' or more* |
| Angle of the main branches | 0% angle to soil line for 15 cm then the branch bends on a 30% angle to soil line | 85% angle to the soil line |
| Diameter of branches | 1 cm | 1 cm |
| Average number of leaves per main branch | 30 | 28 |
| Range of internode length of main branch | 1 to 2 cm | .5 to 1.5 cm |
| Average sub-branches per main branch | 8 | 4.5 |
| Average internode length on sub-branch | .7 to 1.2 cm | .5 to 1 cm |

-continued

| | 'HINES DARKLEAF' | 'BALLERINA' |
|---|---|---|
| Average number of leaves per sub-branch | 10 | 7 |
| Foliage: | | |
| Shape of leaves | elliptic to obovate | obovate to oblanceolate |
| Margins | recurved entire | undulate |
| Apex | cuspidate | acute |
| Base | narrow cuneate | attenuate |
| Average size of leaf | length 8.0 cm, width 3.38 cm | length 6.5 cm, width 2.7 cm |
| Type of leaves | simple | simple |
| Surface texture | glabrous, coriaceous | coriaceous |
| Winter Foliage Color: | | |
| Upper surface of mature leaf | RHS 187A, greyed purple with black undertones | RHS 137A |
| Lower surface of mature leaf | RHS 138A | RHS 142B |
| Upper surface of juvenile leaf apex | RHS 59A | RHS 178B |
| Upper surface of juvenile leaf base | RHS 143A | RHS 178B |
| Lower surface of juvenile leaf | RHS 143C | RHS 176C |
| Summer Foliage Color: | | |
| Upper surface of mature leaf | RHS 147A | 1060/1 pg. 200, ivy green* |
| Lower surface of mature leaf | RHS 146B | 960/3 pg. 187, spinach green |
| Upper surface of juvenile leaf | RHS 178C changing to 164A | ** |
| Average petiole length | 1.4 cm | .7 cm |
| Flower: | | |
| Blooming habit | February to late April, peak time March to mid-April; sporadic blooms in September to November in Houston, Texas | February to May; peak time April to May; sporadic blooms in August to October* February to late April, peak time March to mid-April; sporadic blooms in September to November in Houston, Texas |
| Shape of inflorescence | linear panicle | broad pyramidal panicle |
| Average length and description of panicle | 10.3 cm, slightly hairy | 9.8 cm, slightly hairy |
| Color of peduncle | apex RHS 143C, base 59A | RHS 184A |
| Range of pedicel per peduncle | 13.6 | 16.25 |
| Range of flowers per pedicel | 1 to 2 | 1 |
| Shape of flower and average size | rotate; 2.1 cm in diameter | rotate; 2.4 cm in diameter |
| Number of petals | 5 | 5 |
| Petal shape | ovate (curled) | obovate |
| Overall color of flower | single bicolor pink petals with a circle of white surrounding the yellow stamens; as the flower matures the outer edge of the petals begins to turn white | single solid pink, pink petals with yellow stamens |
| Petal color | RHS 54C, 155C | RHS 55B |
| Average number of stamens per | 19.4 | 19 |

-continued

| | 'HINES DARKLEAF' | 'BALLERINA' |
|---|---|---|
| flower | | |
| Average stamen length | .6 cm | .7 cm |
| Stamen color | new anther | |
| | RHS 10B | RHS 10B |
| | new filament | |
| | RHS 155C | RHS 155C |
| | old anther | |
| | RHS 162A | RHS 162A |
| | old filament | |
| | RHS 59D | RHS 59D |
| Style/flower | 2 | 2 |

-continued

| | 'HINES DARKLEAF' | 'BALLERINA' |
|---|---|---|
| Color of style | RHS 160B | RHS 160B |
| Sepals | 5 united | 5 united |

All information taken on Rhaphiolepis 'Hines Darkleaf' and 'Ballerina' was collected from comparable plant material of similar size and age at Hines Nursery in Houston, Texas unless otherwise stated.

*Information taken from Plant Patent 2,972

**Information not published in Plant Patent 2,972

I claim:

1. A new and distinct variety of *Rhaphiolepis indica* plant substantially as herein shown and described, and which is particularly characterized by its dark purple winter foliage and compact, low, prostrate growth habit.

* * * * *

UNITED STATES PATENT AND TRADEMARK OFFICE

CERTIFICATE OF CORRECTION

PATENT NO. : Plant 8,635

DATED : March 8, 1994

INVENTOR(S) : William C. Barr

It is certified that error appears in the above-indentified patent and that said Letters Patent is hereby corrected as shown below:

On the Title Page:

Item [56] References Cited, U.S. PATENT DOCUMENTS, after "[58]" insert the following reference:
-- [56] Reference Cited
U.S. PATENT DOCUMENT
P.P. 2,972 6/1970 Bordier...Plt. 67.5 --.

Column 1, line 5, change "Indiana" to -- Indian --.
Column 1, line 11, change "new found" to -- newfound --.

Column 3, line 53, change "0% angle" to -- 0° angle --.
and change "85% angle" to -- 85° angle --.
Column 3, line 55, change "30%" to -- 30° --.

Signed and Sealed this

First Day of November, 1994

Bruce Lehman

*Attest:*

BRUCE LEHMAN

*Attesting Officer*

*Commissioner of Patents and Trademarks*